(12) United States Patent
Hansen et al.

(10) Patent No.: US 12,564,231 B2
(45) Date of Patent: Mar. 3, 2026

(54) CHARGER POSITIONING BELT

(71) Applicant: Galvani Bioelectronics Limited, Brentford (GB)

(72) Inventors: Morten Hansen, Brentford (GB); Jay Canham, Brentford (GB)

(73) Assignee: Galvani Bioelectronics Limited, Stevenage (GB)

( * ) Notice: Subject to any disclaimer, the term of this patent is extended or adjusted under 35 U.S.C. 154(b) by 420 days.

(21) Appl. No.: 17/769,620

(22) PCT Filed: Oct. 15, 2020

(86) PCT No.: PCT/US2020/070670
§ 371 (c)(1),
(2) Date: Apr. 15, 2022

(87) PCT Pub. No.: WO2021/077138
PCT Pub. Date: Apr. 22, 2021

(65) Prior Publication Data
US 2023/0041002 A1 Feb. 9, 2023

Related U.S. Application Data

(60) Provisional application No. 62/926,163, filed on Oct. 25, 2019, provisional application No. 62/923,109, filed on Oct. 18, 2019.

(51) Int. Cl.
| | |
|---|---|
| *A41F 9/02* | (2006.01) |
| *A41D 1/00* | (2018.01) |
| *A41F 9/00* | (2006.01) |
| *A61B 5/00* | (2006.01) |

(52) U.S. Cl.
CPC .............. *A41F 9/025* (2013.01); *A41D 1/002* (2013.01); *A41F 9/002* (2013.01); *A61B 5/6831* (2013.01)

(58) Field of Classification Search
CPC .... A41F 9/025; A41F 9/02; A41F 9/00; A41F 9/002; A41F 9/005; A41F 9/007; A61B 5/6831
See application file for complete search history.

(56) References Cited

U.S. PATENT DOCUMENTS

| | | | | |
|---|---|---|---|---|
| 959,952 | A | * | 5/1910 | Melen .................... A41F 9/025 |
| | | | | 24/351 |
| 1,601,173 | A | * | 9/1926 | Hill ......................... A41F 9/002 |
| | | | | 2/322 |
| 2,342,210 | A | * | 2/1944 | Murphey ............... A44B 11/20 |
| | | | | 2/322 |

(Continued)

FOREIGN PATENT DOCUMENTS

| | | |
|---|---|---|
| JP | 2008142222 A | 6/2008 |

OTHER PUBLICATIONS

Extended European Search Report received for EP Serial No. 20876441.5 on Sep. 15, 2023, 9 pgs.

(Continued)

*Primary Examiner* — Uyen T Nguyen
(74) *Attorney, Agent, or Firm* — Merchant & Gould P.C.

(57) ABSTRACT
A belt-like garment is disclosed herein that addresses the need in the wireless recharging field for a holder that maintains the proximity of the recharger to the implanted device, is less bulky and better conforming to the wearer, is easy to don and doff, and prevents shifting throughout the recharging session.

20 Claims, 10 Drawing Sheets

(56)                References Cited

U.S. PATENT DOCUMENTS

| | | | | |
|---|---|---|---|---|
| 3,040,331 A * | 6/1962 | Lampkowitz | ........... | A41F 9/025 |
| | | | | 2/243.1 |
| 4,709,692 A * | 12/1987 | Kirschenberg | .......... | A61F 5/028 |
| | | | | 450/114 |
| 4,991,234 A * | 2/1991 | Greenberg | .............. | A61F 5/028 |
| | | | | 2/920 |
| 5,263,202 A * | 11/1993 | Siberell | ................. | F16G 11/101 |
| | | | | 24/713.2 |
| 5,396,906 A * | 3/1995 | Harrold | ................... | A61F 5/028 |
| | | | | 602/19 |
| 5,548,871 A * | 8/1996 | Trethewey | ............. | A44B 18/00 |
| | | | | 24/442 |
| 5,577,306 A * | 11/1996 | Gold | ......................... | A41F 1/06 |
| | | | | 24/712 |
| 6,073,270 A * | 6/2000 | Schnabl | .................. | A41F 9/025 |
| | | | | 2/237 |

| | | | | |
|---|---|---|---|---|
| 9,713,544 B2 * | 7/2017 | Barbosa | .................. | A61F 5/026 |
| 2007/0232973 A1 * | 10/2007 | Serola | ................... | A61F 5/0193 |
| | | | | 2/908 |
| 2009/0082835 A1 * | 3/2009 | Jaax | ........................ | H02J 50/10 |
| | | | | 607/61 |
| 2012/0012630 A1 * | 1/2012 | Lui | ......................... | A41F 9/002 |
| | | | | 224/660 |
| 2012/0259261 A1 | 10/2012 | Clark | | |
| 2013/0211772 A1 * | 8/2013 | Ross, Jr. | .............. | A61B 5/1118 |
| | | | | 702/141 |
| 2013/0303956 A1 | 11/2013 | Anglada | | |

OTHER PUBLICATIONS

International Search Report and Written Opinion for Application No. PCT/US20/70670, mailed on Jan. 5, 2021, 7 pages.

* cited by examiner

Provide elastic fabric band          402

Attach pocket with grip          404

Attach hook-and-loop components          406

Add slider          408

Affix proximal end to distal end          410

400

Position garment around body — 502

Tighten slider — 504

Affix hook-and-loop fastener — 506

Insert recharger into pocket — 508

Position pocket proximate to implanted device — 510

500

CHARGER POSITIONING BELT

RELATED APPLICATION

The present application is a National Phase entry of PCT Application No. PCT/US2020/070670, filed Oct. 15, 2020, which claims the benefit of U.S. Provisional Application No. 62/923,109 filed Oct. 18, 2019, and U.S. Provisional Application No. 62/926,163, filed Oct. 25, 2019, each of which is hereby incorporated herein in its entirety by reference.

TECHNICAL FIELD

Embodiments disclosed herein relate to wireless recharging systems, such as those used for implanted medical devices. In particular, garments are disclosed herein that maintain physical arrangements between wireless rechargers and corresponding implanted devices throughout the duration of a recharging session.

BACKGROUND

Devices that recharge wirelessly are rapidly becoming more prevalent, in a variety of fields from telecommunications to transportation and for medical devices, among others. For medical devices in particular, wireless recharging provides significant advantages to conventional, direct charging, because patients may be provided with implanted devices that are not easily accessible.

Typically, a wirelessly rechargeable implanted medical device will be equipped with an antenna or receiver that can transform a received electromagnetic signal into charge current to power the device, recharge an onboard battery, or both. The recharger (i.e., an external source of electromagnetic field) is positioned so that the implanted device can receive sufficient charge from the electromagnetic field to recharge. In general, a higher recharge rate requires that the implanted device and the recharger be positioned relatively close to one another, and the relative position of the recharger and the implanted device should ideally remain within this proximity for the duration of the recharging session.

Often, the period of time required for full recharge of an implanted medical device can exceed the amount of time that a wearer may wish to physically hold the recharger in the appropriate position for recharging. While some rechargeable medical devices can require only about 10 minutes to fully recharge, others can require up to several hours. In order to reduce the obtrusiveness of such systems to the wearer, various holding mechanisms have been proposed that a user can wear during recharge sessions. Such garments and mechanisms are often bulky, burdensome to don or doff, and can shift throughout the recharging session leading to reduced charging efficiency (or even loss of recharge entirely).

SUMMARY

A belt-like garment is disclosed herein that addresses the need in the wireless recharging field for a holder that maintains the proximity of the recharger to the implanted device, is less bulky and better conforming to the wearer, is easy to don and doff, and prevents shifting throughout the recharging session.

The belt-like garment comprises a pre-formed loop with features for adjustment of the size of the loop. The size of the loop may be adjusted without breaking the pre-formed loop.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
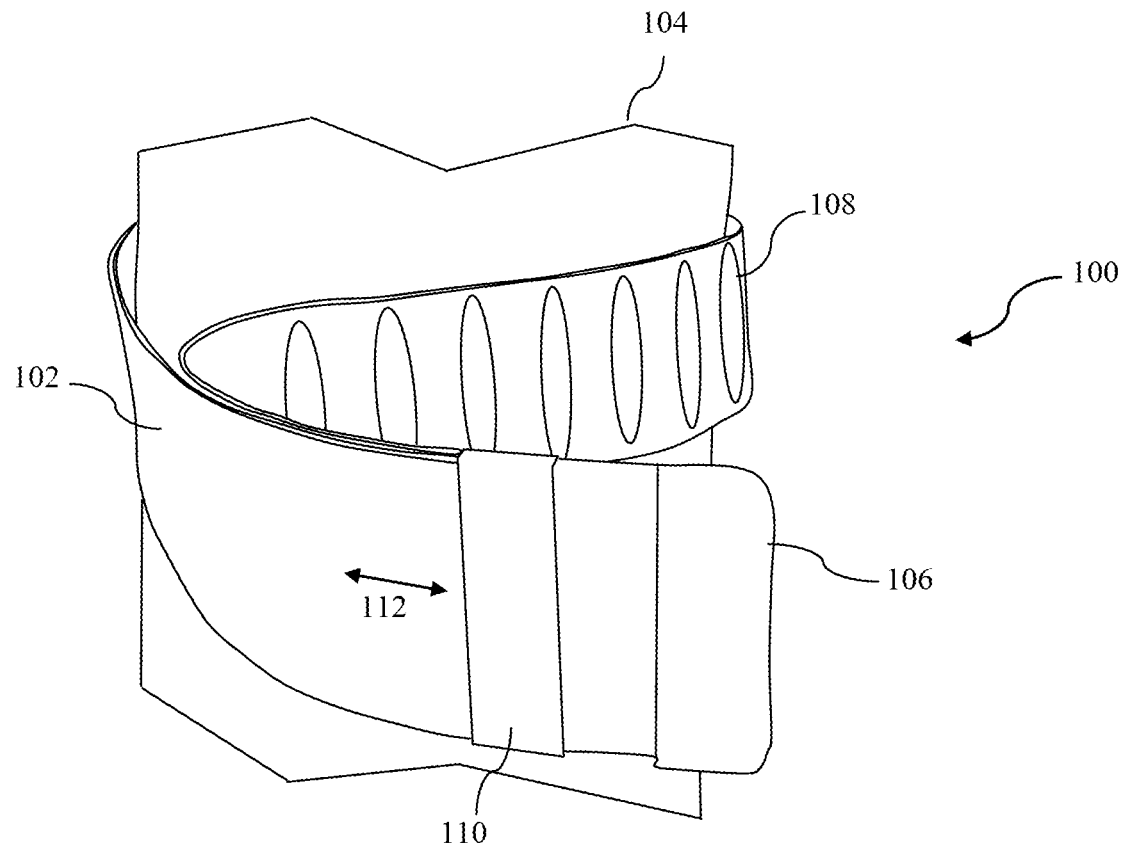
FIG. 1 is a perspective view of an embodiment of a garment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments described herein include garments and methods for using them that solve the aforementioned problems with recharging implanted medical devices. Improving patient comfort and ease of use with recharging devices can have positive effects on compliance with treatment programs, and promotes better health for patients having implanted devices while at the same time reducing the intrusion that recharging could otherwise have on their daily lives.

As shown in FIG. 1, a garment 100 is made of a belt/band 102 made of a stretch knit fabric, for example nylon and spandex mix, or another stretchable material. The belt 102 circumscribes a patient 104 in use. In some embodiments, the portion of the patient 104 that is circumscribed by the belt 102 could be a torso, such as the portion of the torso including the thorax, where implanted devices are often positioned. It should be understood, however, that the garment 100 could be resized or reshaped in order to fit with any other portions of the anatomy of the patient 104.

As shown in FIG. 1, in its assembled state the garment 100 is a loop. In other words, belt 102 circumscribes the patient 104 and is affixed to itself to form a band. Once the garment 100 is fully assembled during manufacture, the garment 100 forms the loop/band, and remains in the unbroken loop form. At the end of belt 102 where the two ends are connected (joined together during manufacture) with one another is a tab 106. The tab 106 includes one half of a fixation system, which is hook-and-loop in the embodiment shown in FIG. 1. It will be understood that various other fixation mechanisms could be used in alternative embodiments. Hook and loop systems are preferred for some patients where dexterity is limited, such as patients with limited dexterity. The applicant has recognized that there is a need for simpler fastening mechanisms among patients who have implanted, rechargeable devices as well as inflammatory disorders such as rheumatoid arthritis. Hook and loop serve such patients well, because the connection system does not require significant dexterity to connect. Further, as the garment 100 is already in a loop form, unlike a typical wearable belt, the user is able to more easily don and adjust the garment 100.

In one embodiment, the hook (or micro-hook) portion of the fastening mechanism is arranged on tab 106, while the loop portions are arranged in loop segments 108 spaced along the belt 102. Belt 102 can be made of an elastic or stretchable material, and by separating the loop segments 108 (which may not be stretchable) into different sections, the length of the overall garment 100 can be stretched to provide sufficient compressive force on the patient 104 to avoid significant movement after donning.

Slider 110 is arranged around both ends of belt 102 at the point where they are coupled to one another proximate the tab 106. Arrow 112 depicts a direction of movement for slider 110, which is free to slide along the belt 102.

In use, the patient 104 (or a caretaker) can arrange the garment 100 such that the belt 102 circumscribes a portion of the patient 104 in which a medical device has been implanted. The patient (or caretaker) can tighten the belt 102 such that it provides sufficient compression to deter movement relative to the patient 104, and then slide the slider 110 in the direction 112. The tab 106 can then be affixed to a corresponding one of the loop segments 108. None of these steps requires significant hand dexterity, and yet the garment 100 is efficiently and securely coupled to the wearer. Furthermore, because the entire garment 100 is then flush with the body of the patient 104, the garment 100 is not obtrusive or cumbersome to the patient 104 as he or she goes about daily activities.

Figure 2:
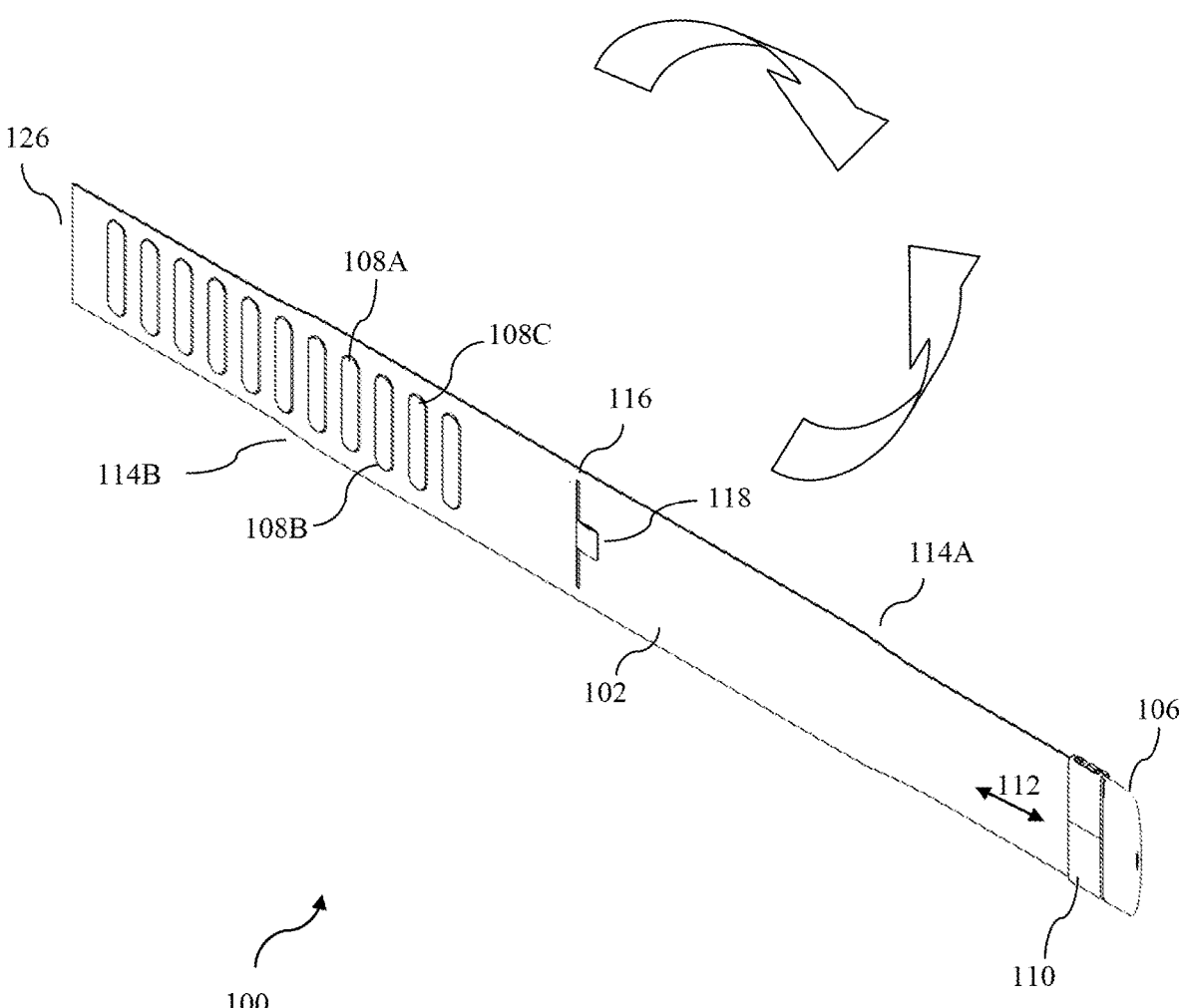
FIG. 2 is a top view of the garment of FIG. 1, shown in a disassembled state during manufacture.

FIG. 2 depicts the garment 100 in a disassembled state with at least one manufacturing step, such as affixing proximal and distal ends together, yet to be completed to assemble the garment 100. In this disassembled state, further components of the garment 100 are visible, in addition to those previously described with respect to FIG. 1.

For example, in the view shown in FIG. 2 it can be seen that there are eleven distinct loop segments (three of which, 108A, 108B, and 108C, are labeled individually). Furthermore, the insertion mechanism for a recharger (not shown) into the garment 100 can be seen in this view.

Shoulders 114A and 114B are more readily visible in FIG. 2 than in FIG. 1. Shoulders 114A provide extra width W1 for the garment 100 adjacent to a pocket (120, FIG. 3) than elsewhere, where garment 100 has width W2. The relatively larger width W1 can be selected to prevent a recharger from shifting, as will be apparent from the view shown in FIG. 3. In one embodiment, a recharger is substantially cylindrical, having a diameter of 4 inches, and width W1 is slightly more than 4 inches while width W2 is slightly less than 4 inches.

Slit 116 is arranged in the belt 102, and has a width sufficient to permit the insertion of a particular recharger therein. In embodiments where belt 102 is made of an elastic material, slit 116 may be slightly undersized relative to the recharger, to prevent the recharger from falling out of the garment 100.

Grip 118 is an optional component of garment 100, and can assist a wearer or caretaker to open the slit 116 for insertion of a recharger. Grip 118 can be sufficiently large and grippable for patients with limited dexterity to use in order to open the slit 116 without requiring interaction with more complex devices such as zippers, snaps, or buttons, and is also less bulky than those conventional fasteners.

In FIG. 2, which illustrates the garment 100 during manufacture prior to completion of assembly, garment 100 is shown with the two ends of the belt disconnected, rather than coupled at tab 106 as shown in FIG. 1. The arrows in FIG. 2 show a folding pattern that could be used to connect a distal end 126 of the garment 100 to the portion of the belt 102 adjacent tab 106, resulting in the final manufactured shape (i.e. loop/band with the ends of the belt 102 affixed together so that the garment remains as loop/band where the loop/band is not broken during normal use by a user in one embodiment) described previously with respect to FIG. 1.

Figure 3:
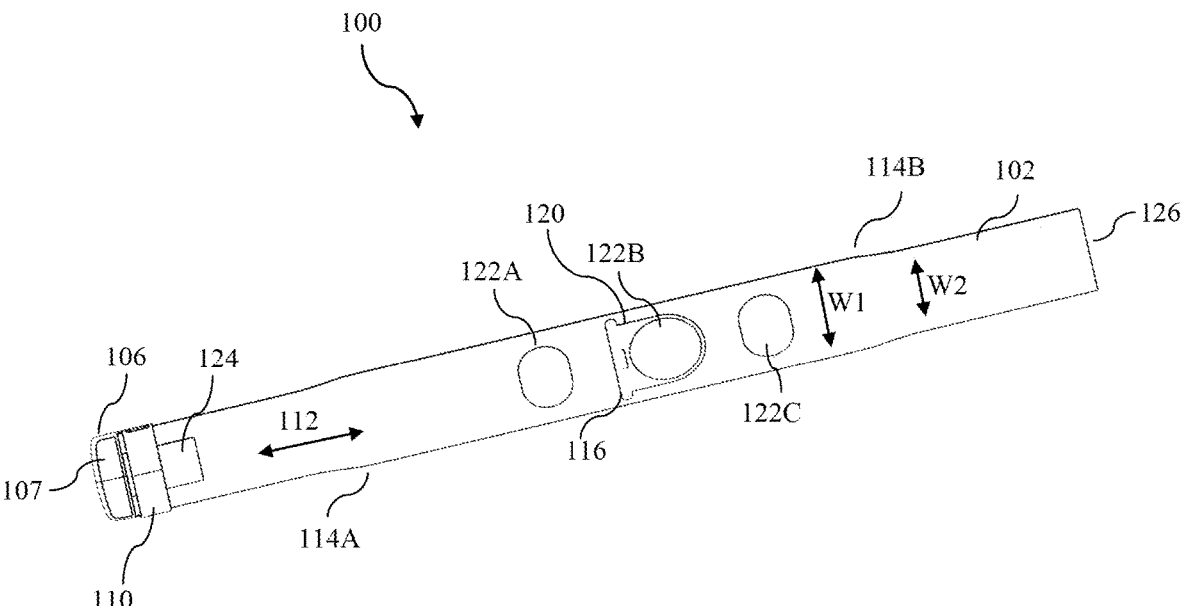
FIG. 3 is a bottom view of the garment of FIG. 1, shown in the disassembled state during manufacture.

FIG. 3 shows the garment 100 of FIGS. 1 and 2, this time depicting the side that is configured to face the patient 104 (FIG. 1). As shown in FIG. 3, the garment 100 includes the tab 106 with hook section 107 for attaching to the loop sections 108 (FIGS. 1, 2). FIG. 3 further depicts pocket 120, which is configured to hold a recharger. Slit 116 forms an entryway to the pocket 120.

Three optional grip pads 122A, 122B, and 122C are arranged on and around the pocket 120 to provide enhanced friction between the wearer and the garment 100. These grip pads 122A, 122B, and 122C are made of a material, for example thermoplastic polyurethane, that has some tackiness or grippiness, such that there is a high coefficient of static friction between those portions of the garment 100 and the patient or their clothing. In this way, the grip pads 122A, 122B, and 122C provide a second mechanism for keeping the recharger arranged proximate to an implanted device (the first being the compressive force provided by the stretched elastic belt 102, as described above). In alternative embodiments, the garment 100 could include one, two, or any other number of grip pads (e.g., 122A-122C). In alternative embodiments, grip pads could be arranged on the inner side of the belt 102, or on the pocket 120.

Patch 124 is an optional product label.

In embodiments the distal end 126 could be attached by stitching, stapling, gluing or other permanent fasteners to the proximal end portion of belt 102 (i.e., nearby to patch 124) to form a loop/band as shown in FIG. 1. In other embodiments the distal end 126 could be attached to the proximal end portion of the belt by semi-permanent fasteners. Semi-permanent fasteners, such as hook and loop fasteners or others that couple components together in a releasable manner, can be used to semi-permanently affix one component to another. Therefore, the garment 100 may be provided to the user in a non-final assembly form.

Figures 4A, 4B:
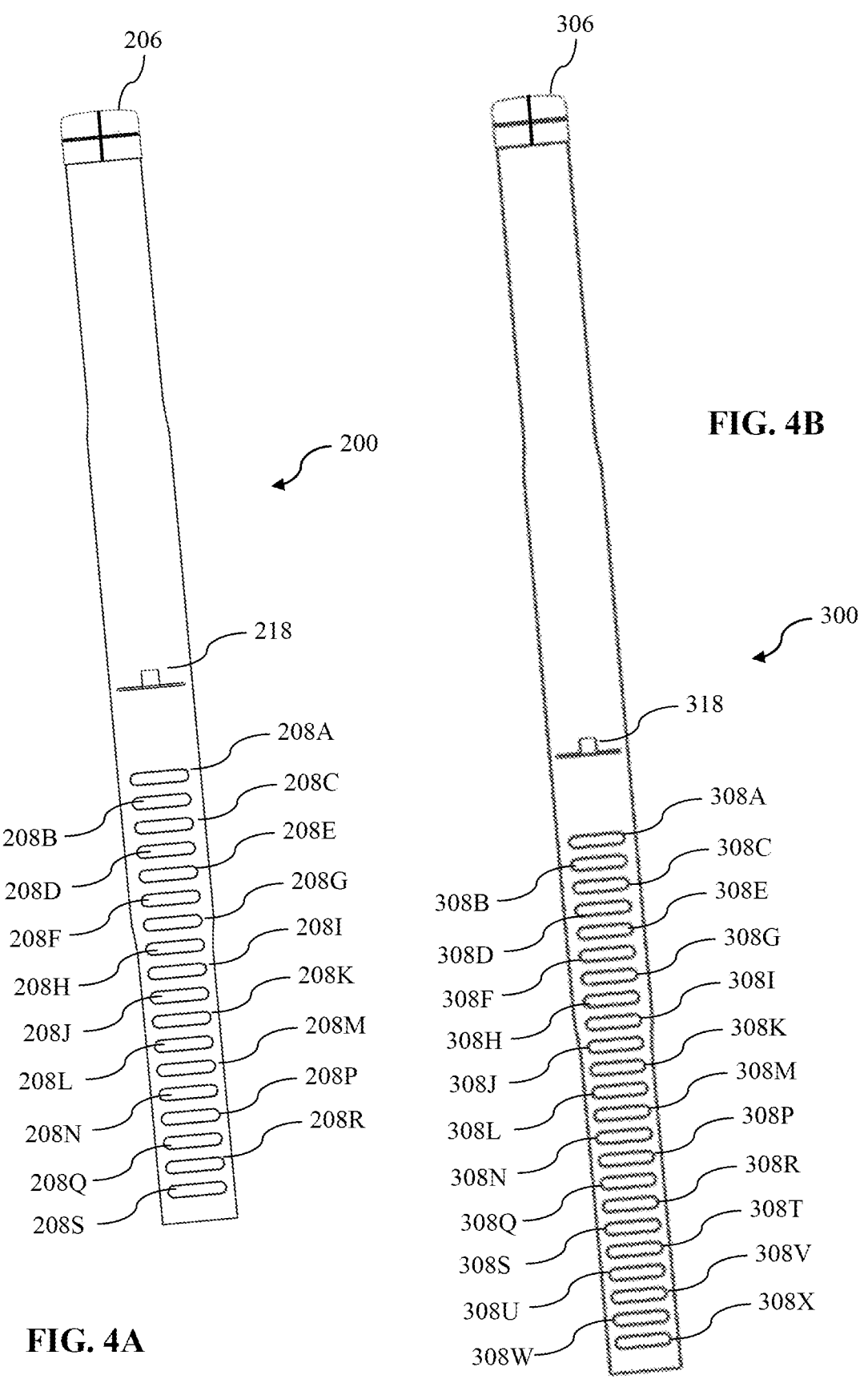
FIGS. 4A and 4B are top views of two further embodiments of garments, each shown in disassembled state during manufacture.

FIGS. 4A and 4B depict two alternative embodiments, garment 200 and garment 300 respectively. Each of the garments 200 and 300 is similar to the garment 100 described above with respect to FIGS. 1-3, except that they have a different length. Garment 200 of FIG. 4A is somewhat longer than garment 100 of FIGS. 1-3, while garment 300 of FIG. 4B is substantially longer than garment 100 of FIGS. 1-3. Although the drawings are not shown to scale, this difference in length can be seen by the relatively larger numbers of loop segments. Garment 200 of FIG. 4A includes eighteen loop segments (208A, 208B, 208C, 208D, 208E, 208F, 208G, 208H, 208I, 208J, 208K, 208L, 208M, 208N, 208P, 208Q, 208R, 208S). Garment 300 of FIG. 4B includes twenty-three loop segments (308A, 308B, 308C, 308D, 308E, 308F, 308G, 308H, 308I, 308J, 308K, 308L, 308M, 308N, 308P, 308Q, 308R, 308S, 308T, 308U, 308V, 308W, 308X). The other components of garments 200 and 300 are substantially the same as their counterparts in FIGS. 1-3, with reference numbers iterated by a factor of 100 (e.g., grips 218 and 318 are substantially similar to grip 118 of FIG. 2, and tabs 206 and 306 are substantially similar to tab 106 of FIGS. 1-3).

Figures 5A, 5B:
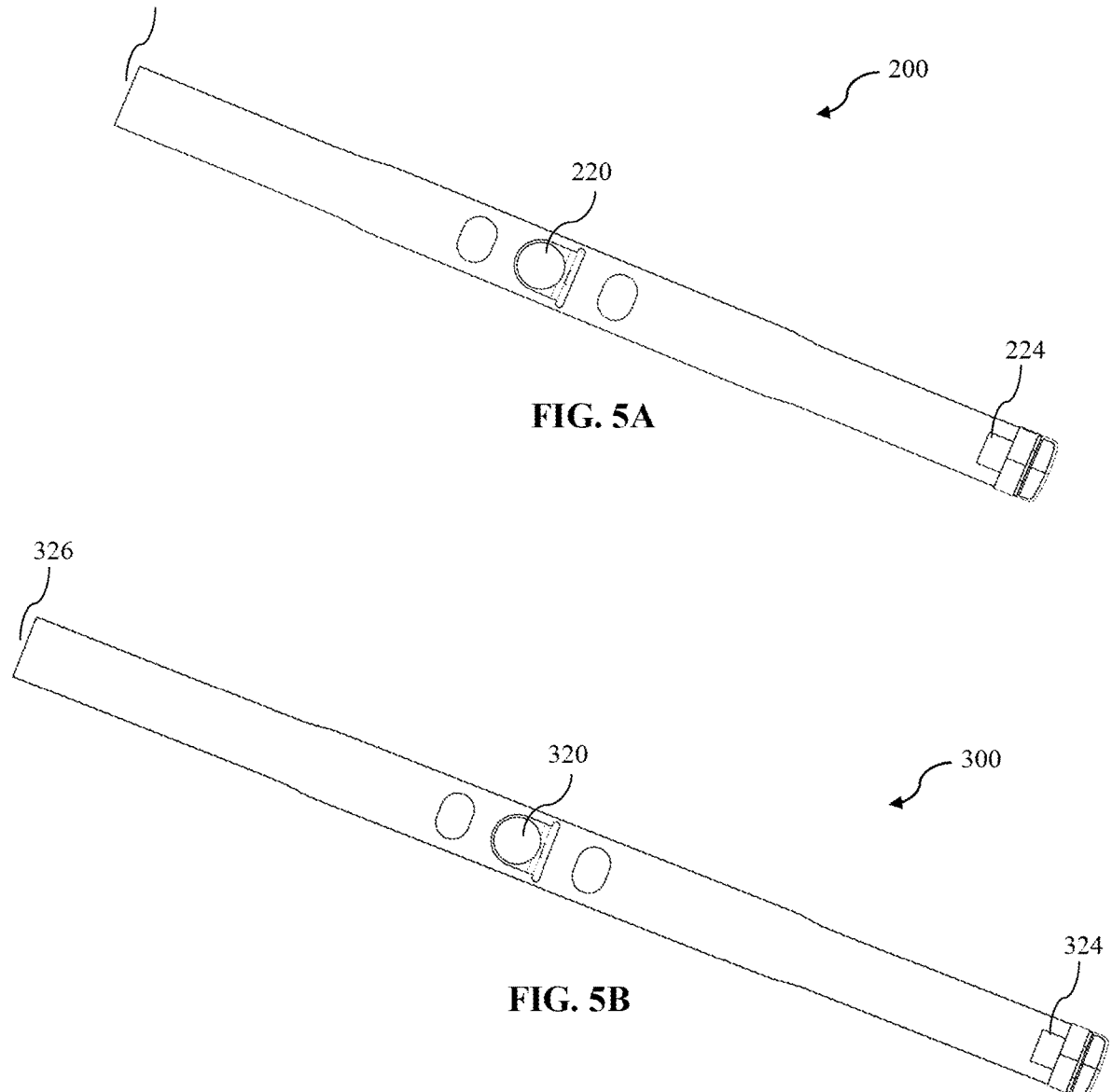
FIGS. 5A and 5B are bottom views of the garments of FIGS. 4A and 4B, respectively.

FIGS. 5A and 5B are alternative views of the garments shown in FIGS. 4A and 4B, respectively, depicting the sides thereof that are adjacent a patient in use. Once again, components of FIGS. 5A and 5B have reference numbers iterated by factors of 100 from their counterparts in FIGS. 1-3. Pockets 220 and 320 can be substantially the same as their counterpart 120, and patches 224 and 324 are product labels. Distal ends 226 and 326 are coupled to the proximal end portions, respectively, in the same way that distal end 126 can be affixed to the proximal end portion as described above with respect to FIG. 3.

Figure 6:
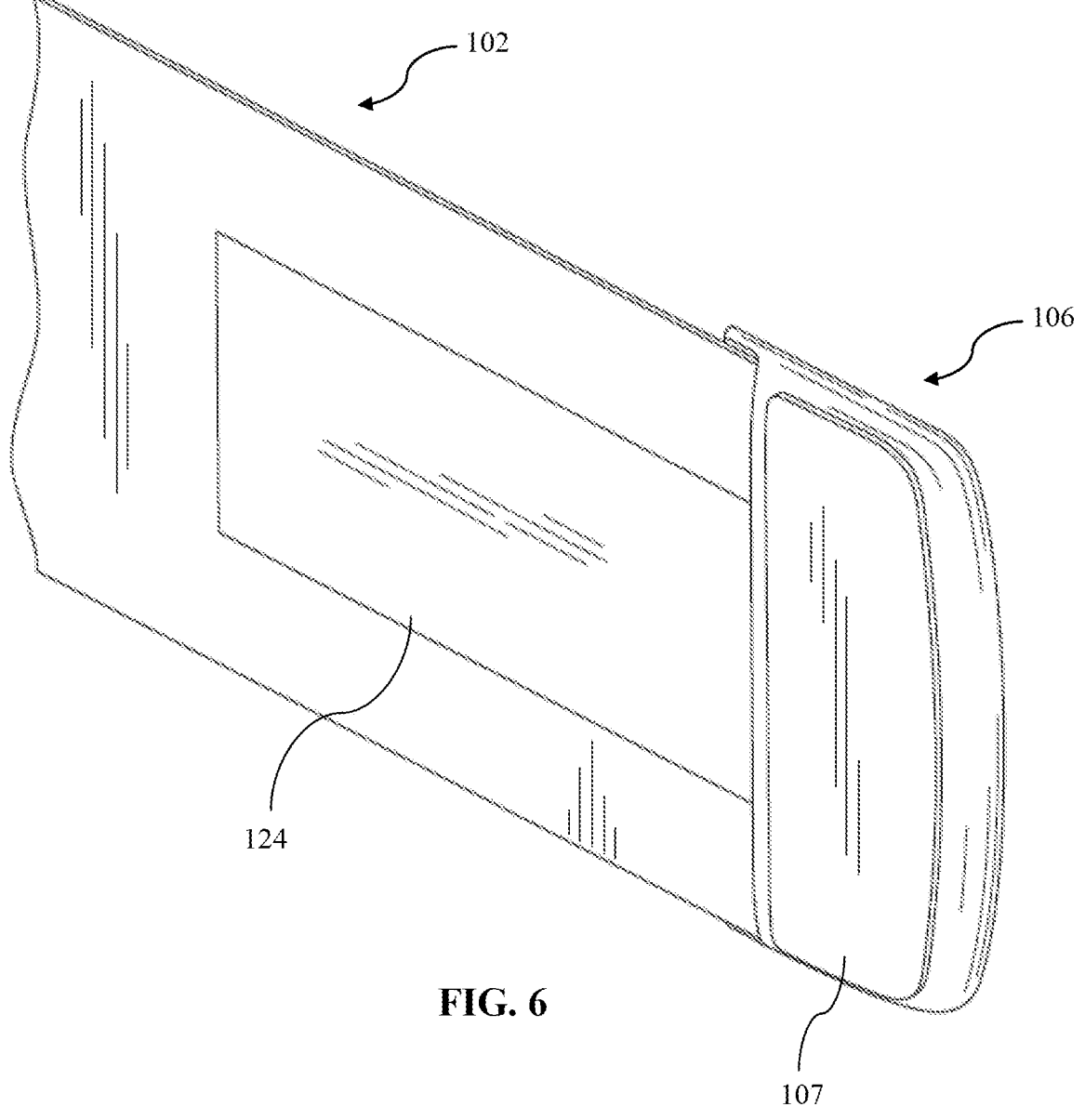
FIG. 6 is a detailed view of a tab and belt, according to an embodiment.

FIG. 6 is a detailed view of a portion of the garment 100, in particular showing the connection between tab 106 and belt 102. As depicted in FIG. 6, only one end of belt 102 is coupled to the tab 106, and those two components are permanently fixed to one another. Label 124 is shown extending from tab along belt 102, though as described above this component is optional. In its place, in some embodiments, is a semi-permanent affixing system, such as hook-and-loop, that permits selective attachment of the other end of the belt 102 thereto. When the two ends are coupled to one another, the belt 102 is arranged in a round configuration as shown, for example, in FIGS. 9A-9C below, or FIG. 1 above.

FIG. 6 shows the relative thicknesses and widths of the tab 106 and the belt 102. As shown in FIG. 6, the thickness of tab 106 is larger than that of the belt 102, and even more than double the thickness of belt 102. In this way, slider 110 is prevented from falling off the end of the garment 100 at tab 106, because the outer diameter of the tab 106 is larger than the inner diameter of the slider 110.

Furthermore, FIG. 6 shows the width (i.e., top to bottom direction in the orientation shown in FIG. 6) of the fastener 107. In embodiments, the width of fastener 107 can be as large or even larger than the width of belt 102. As such, the width of fastener 107 can be larger than a width of the corresponding fasteners (e.g., 108) to which fastener 107 may be coupled. In fact, fastener 107 can be made larger in both width and length than the corresponding fasteners (108) in order to make fastening the device easier. The width of fastener 107 can be made larger in width than a gap between the corresponding fasteners (108), such that the positioning of fastener 107 does not have to be immediately above a corresponding fastener 108. In other words, regardless of the positioning of the fastener 107 along the belt body with any fasteners 108, the fastener 107 will necessarily at least partially overlap with one or more corresponding fastener 108.

Figure 7:
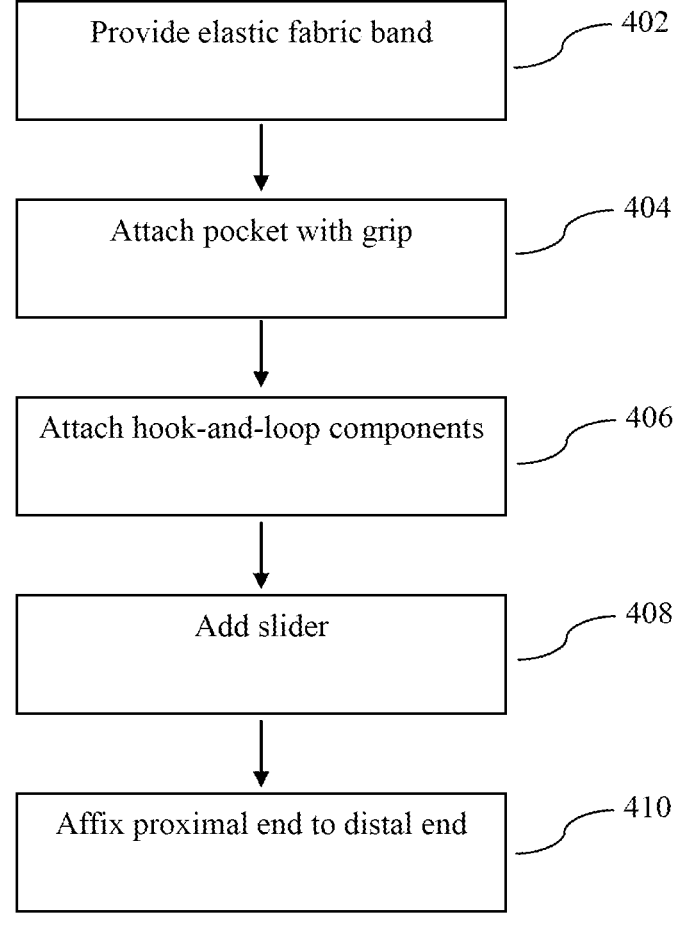
FIG. 7 is a flowchart describing a method for assembling the garments of FIGS. 1-5.

FIG. 7 is a flowchart of a manufacturing method 400 for providing a garment as described herein.

At 402, an elastic fabric band is provided. The elastic fabric band can be similar to the belts (102, 202, 302) described herein.

At 404, a pocket with a grip is attached to the band. As shown in the garments described above, the pocket can be arranged on a side of the garment that is intended to be positioned adjacent to a patient, with a slit arranged on the other side for inserting or removing a recharger into the pocket. The grip can be used by a patient or caretaker, including an individual with limited dexterity, to open the pocket even when the fabric is made of an elastic material. Although not shown in FIG. 7, the method 400 can further include providing one or more pads of a material having a high coefficient of static friction (e.g., pads 122A, 122B, 122C) can also be arranged at or around the pocket at 404.

At 406, hook and loop components are added. It should be understood that while the elements of method 400 are shown in order, these steps need not be performed in this exact order—for example, the hook and loop components could be added at 406 before the pocket with grip is added at 404 in an alternative embodiment. The hook and loop components are added at 406 to provide structures that can fix the garment in a closed position, as shown with respect to fasteners 107 and 108.

At 408, a slider is added. The slider can be similar to the slider 110 shown in FIGS. 1-3, and enables a wearer to cinch the garment to a desired tightness level, then maintain that level of tightness with the slider 110 and the hook-and-loop structures added at 406.

At 410, a proximal end of the fabric band is affixed to a distal end of the fabric band. This is shown, for example, in FIG. 1 where the two ends of belt 102 are attached to one another at opposite ends. Additionally, affixing the proximal end and distal end is described with respect to garments 200 and 300 in that the distal ends (226, 326) can be coupled to patches 224 and 324 as described herein.

Affixing the proximal end to the distal end at 410 can include sewing, stitching, stapling, gluing or other permanent or semi-permanent fasteners, and threading both ends through the slider provided at 408. Such a structure is shown, for example, in FIG. 1, in which slider 110 circumscribes two layers of belt 102.

As it will be appreciated by those skilled in the art, the order of some of the manufacturing steps may be changed or swapped around. For example, step 406 may be completed before step 404, or step 410 may be completed before step 408. Further, some additional steps may be provided.

The slider 110 remains on the belt 102 as the tab 106 has a size that makes it impossible for the tab 106 to slide through the slider 110.

According to one embodiment, a method includes providing an elastic fabric band extending along a length from a first end to a second end, the first end permanently affixed to a tab, the elastic fabric band including a middle section that has a width that is larger than a width of the first end and the second end. The method further includes attaching a pocket to the elastic fabric band, wherein: the pocket is configured to receive a wireless recharger device, and the pocket is arranged along a middle section of the elastic fabric band having a width greater than a first end portion and a second end portion thereof. The method further includes attaching a first connector portion to the tab, attaching a plurality of second connector portions to the elastic fabric band, each of the second connector portions configured to engage (for example be semi-permanently attached in a releasable manner) with the first connector portion. The method further includes arranging a slider around both the first end and the second end, and permanently affixing the first end to the tab.

Figure 8:
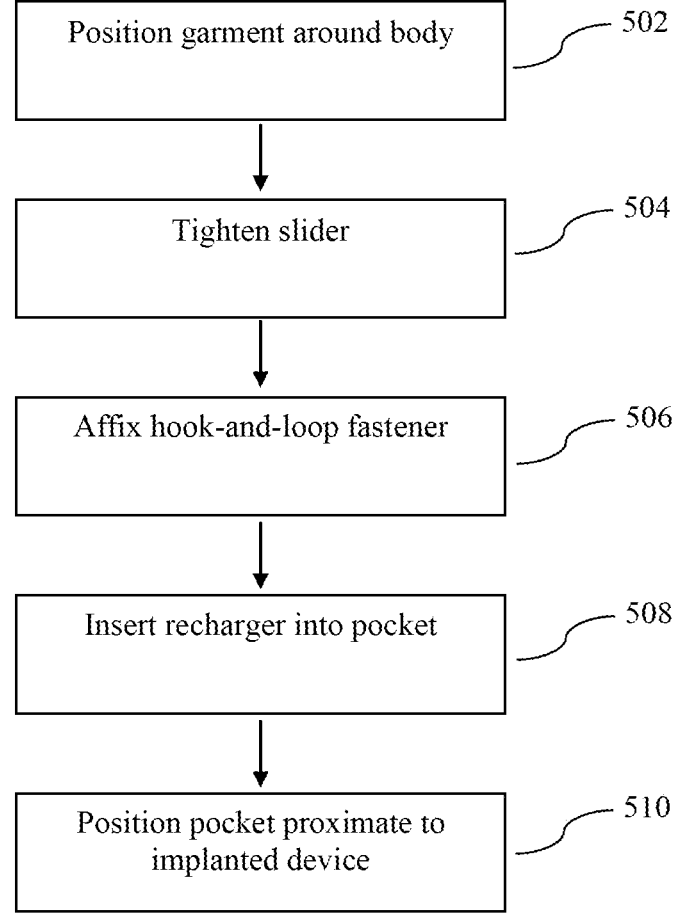
FIG. 8 is a flowchart describing a method for donning the garments of FIGS. 1-5.

FIG. 8 is a flowchart of a method 500 for donning a garment such as those described herein.

At 502, the garment is positioned around the body. For example, as depicted in FIG. 1, garment 100 is positioned around the body 104. The garment can be positioned around the body with sufficient compression to prevent significant relative movement on the body.

At 504, the garment is tightened, by cinching a slider until the garment does not move around on the body easily.

Once the garment is tightened at 504, hook-and-loop fasteners are used to semi-permanently prevent loosening or movement of the garment on the wearer at 506.

At 508, a recharger is inserted into a pocket of the garment. The recharger is thus also maintained adjacent to the body without the possibility for significant movement. Additional movement-prevention mechanisms, including pads (122A, 122B, 122C in FIG. 3) can be present on the garment as well.

At 510, the pocket is positioned proximate to the implanted device. In order to position the pocket proximate to the implanted device, the garment can be loose enough to temporarily allow significant movement between the garment and the wearer.

It will be appreciated that users may have different preferences and different sequences may be used to don and adjust the garment 100.

Each of the elements of the method 500 require very little dexterity, and can be accomplished by individuals for whom conventional devices are unwieldy or simply unworkable. As a result, it is expected that treatment compliance and user satisfaction will be significantly increased.

Figure 9A:
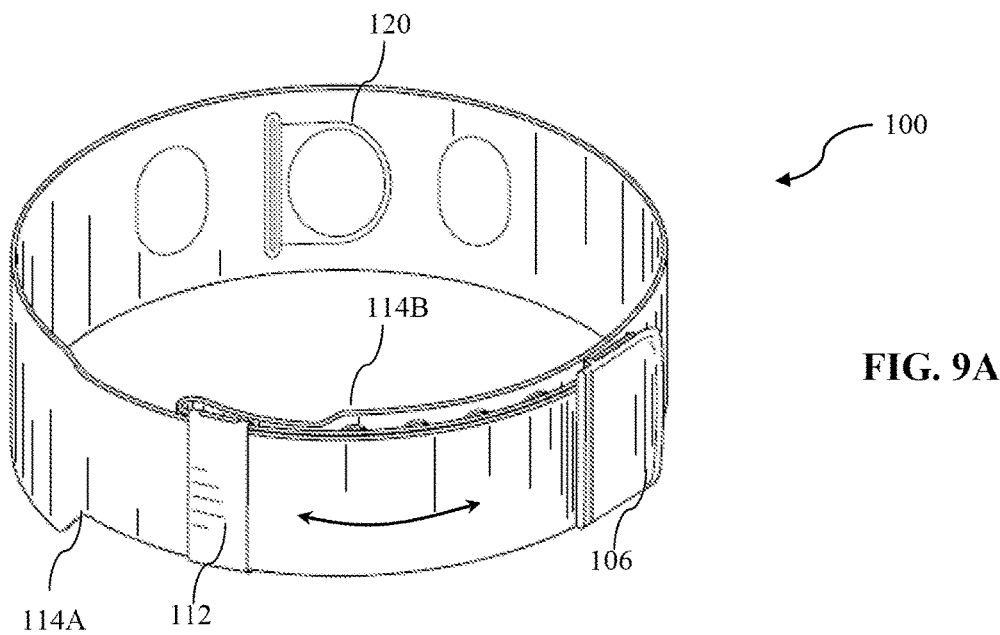
FIGS. 9A-9C depict the garments of FIGS. 2, 4A, and 4B, respectively, in the assembled state.
Figure 9B:
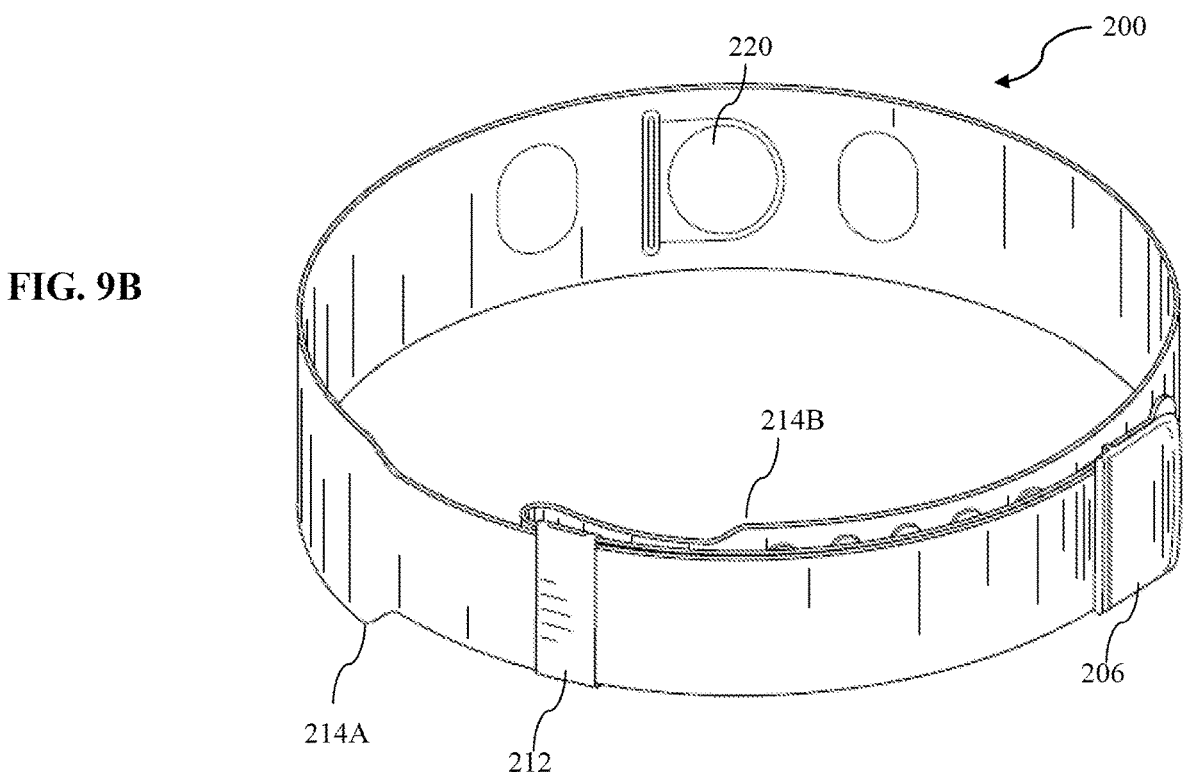
Figure 9C:
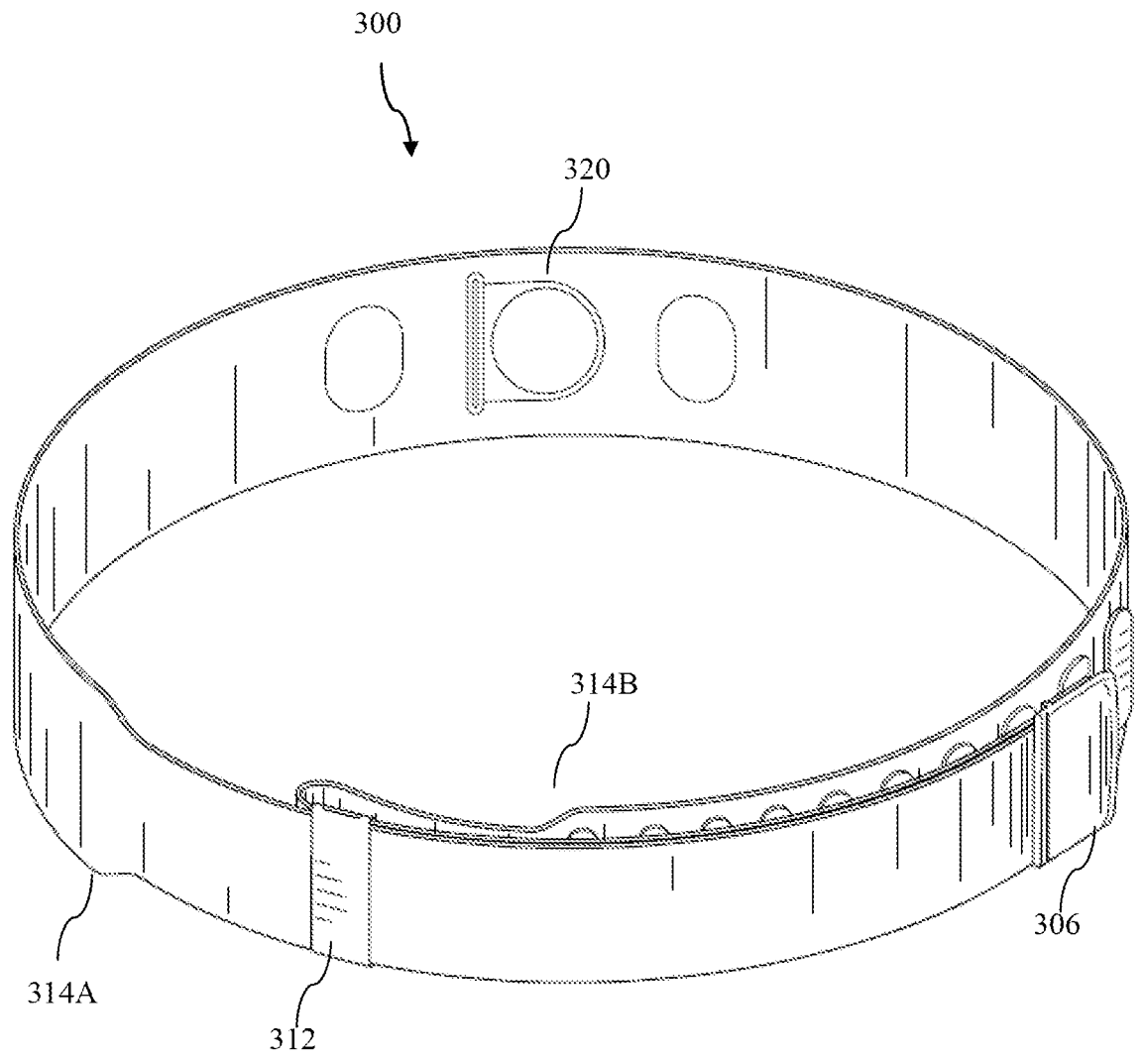

FIGS. 9A-9C depict garments 100, 200 and 300, respectively, in their assembled states. As shown in FIG. 9A by the arrow, similar to the arrow of FIG. 1, the slider 110 can be repositioned along any part of the garment 110 between the shoulders 114A, 114B and the tab 106. By cinching up the slider 110 until the garment is snug, as shown in FIG. 1, and then affixing the tab 106 to a corresponding one of the series of hook-and-loop connectors 108 (FIG. 2), the garment 100 is secured on the user. the slider 110 is arranged around both the first end and the second ends of the garment 100 such that movement of the slider 110 along the belt 102 and away from the tab 106 causes a corresponding decrease in the circumference of the garment.

A recharger can be positioned in the pocket 120, and due to the tightness of fit of the garment 100 as well as the friction from pads 122A, 122B, and 122C, the recharger remains in substantially constant position relative to the patient, proximate an implanted, wirelessly rechargeable device.

Similar components are arranged in garment 200 as shown in FIG. 9B, and in garment 300 shown in FIG. 9C, with like parts having reference numerals iterated by factors of 100. The primary difference between garment 100 of FIG. 8A and garments 200 and 300 of FIGS. 9B and 9C is of size. Garments 100, 200, and 300 are small, medium, and large, respectively, as shown in the drawings and based upon the number of hook-and-loop connectors (although the drawings are not necessarily to scale). It should be understood that any number of other sizes could be used depending on the size of the patient and the portion of the body for which the garment is intended.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A garment comprising:
   a tab having a first connector portion;
   a belt extending along a length from a first end to a second end, the first end permanently affixed to the tab, the belt having a middle section, a first end section extending from the first end towards the middle section, and a second end section extending from the second end towards the middle section, wherein the middle section has a width that is larger than a width of the first end section and the second end section, wherein the belt has an inside surface extending from the first end to the second end and an outside surface extending from the first end to the second end, the inside surface and the outside surface being on opposite sides of the belt;
   a slider having a single opening in which the first end section is received for sliding movement of the slider on the first end section, wherein the slider is configured to receive the second end section of the belt through the single opening for enabling simultaneous sliding movement of the slider on the first and second end sections, wherein the single opening has an inner diameter that is smaller than the width of the middle section such that the slider is not able to slide on the middle section; and
   at least one second connector portion arranged along the belt, the at least one second connector portion configured to be semi-permanently affixed to the first connector portion, wherein the second end section of the belt is configured to be passed through the single opening of the slider by:
(i) moving the second end of the belt relatively towards the first end of the belt while inner surfaces of the first end section and the second end section face each other, and (ii) passing the second end of the belt through the single opening of the slider during the movement, thereby arranging the belt into a first belt state;
wherein the first and second ends of the belt are configured to be affixed together when the garment is in the first belt state such that the inner surfaces of the first and second end sections of the belt face each other, thereby arranging the belt into a second belt state; and
wherein the first connector portion is configured to be semi-permanently affixed to the at least one second connector portion when the garment is in the second belt state such that at least a part of the outside surface of one of the first and second end sections is in opposed facing relationship with at least another part of the outside surface of the first end section, the second end section, or the middle section, thereby arranging the belt into a third belt state.

2. The garment of claim 1, wherein the second end is permanently affixed to the tab in the second belt state.

3. The garment of claim 1, wherein the second end is not affixed to the tab.

4. The garment of claim 3, wherein the second end is configured to be semi-permanently affixed to the first end.

5. The garment of claim 1, wherein the first connector portion and the at least one second connector portion comprises hook-and-loop connectors.

6. The garment of claim 1, further comprising a plurality of second connector portions, and the first connector portion is larger than a gap between adjacent second connector portions of the plurality of second connector portions.

7. The garment of claim 1, further comprising a pocket arranged on the belt, wherein:
the pocket is configured to receive a wireless recharger device; and
the pocket is arranged along the middle section of the belt.

8. The garment of claim 7, wherein the middle section defines a slit, and wherein the pocket is arranged adjacent the slit such that the wireless recharger device can be inserted into the pocket through the slit.

9. The garment of claim 8, further comprising a grip arranged at the slit.

10. The garment of claim 1, wherein the belt includes a first shoulder arranged between the middle section and the first end section, and a second shoulder arranged between the middle section and the second end section.

11. The garment of claim 1, further comprising at least one grip pad arranged on the belt or a pocket.

12. The garment of claim 1, wherein in the first belt state the slider is arranged around both the first end section and the second end section such that movement of the slider along the belt and away from the tab causes a corresponding decrease in a circumference of the garment.

13. The garment of claim 1, wherein the tab has an outer diameter that is greater than the inner diameter of the single opening in the slider, such that the slider is prevented from traveling past the tab.

14. The garment of claim 1, wherein the belt is in the second belt state.

15. The garment of claim 1, wherein the slider comprises only one opening.

16. The garment of claim 1, wherein the at least one second connector portion comprises a plurality of second connector portions that are spaced apart along the length of the belt.

17. The garment of claim 1, wherein the at least one second connector portion is located on the outside surface of the middle section of the belt.

18. The garment of claim 1, wherein the belt is formed into a loop in at least one of the first belt state, the second belt state, and the third belt state.

19. The garment of claim 16, wherein the first connector portion is configured to be semi-permanently affixed to any of the plurality of second connector portions.

20. The garment of claim 1, wherein the at least a part of the outside surface of the first end section is in opposed facing relationship with at least another part of the outside surface of the second end section or the middle section in the third belt state.

* * * * *